(12) United States Patent
Cheng et al.

(10) Patent No.: US 11,690,504 B2
(45) Date of Patent: Jul. 4, 2023

(54) AUTOMATED ENDOSCOPE REPROCESSING UNIT WITH IN-LINE PERACETIC ACID SENSOR

(71) Applicant: Medivators Inc., Minneapolis, MN (US)

(72) Inventors: Karl Cheng, Corona, CA (US); Shelly R. Michaels, Beaumont, CA (US); William D. Michaels, Beaumont, CA (US)

(73) Assignee: Medivators Inc., Minneapolis, MN (US)

( * ) Notice: Subject to any disclaimer, the term of this patent is extended or adjusted under 35 U.S.C. 154(b) by 438 days.

(21) Appl. No.: 16/849,635

(22) Filed: Apr. 15, 2020

(65) Prior Publication Data
US 2020/0329957 A1    Oct. 22, 2020

Related U.S. Application Data

(60) Provisional application No. 62/836,906, filed on Apr. 22, 2019.

(51) Int. Cl.
| A61B 1/12 | (2006.01) |
| A61B 90/70 | (2016.01) |
| A61L 2/18 | (2006.01) |
| A61L 2/28 | (2006.01) |
| B08B 9/032 | (2006.01) |

(52) U.S. Cl.
CPC .............. *A61B 1/125* (2013.01); *A61B 1/123* (2013.01); *A61B 90/70* (2016.02); *A61L 2/186* (2013.01); *A61L 2/28* (2013.01); *B08B 9/0321* (2013.01); *A61B 2090/701* (2016.02); *A61B 2090/702* (2016.02); *A61L 2202/14* (2013.01); *A61L 2202/24* (2013.01)

(58) Field of Classification Search
None
See application file for complete search history.

(56) References Cited

U.S. PATENT DOCUMENTS

| 4,592,785 | A | 6/1986 | Reinert et al. |
| 5,788,925 | A | 8/1998 | Pai et al. |
| 5,834,313 | A | 11/1998 | Lin et al. |
| 5,882,590 | A | 3/1999 | Stewart et al. |
| 6,394,111 | B1 | 5/2002 | Jacobs et al. |
| 6,454,874 | B1 | 9/2002 | Jacobs et al. |
| 6,793,880 | B2 | 9/2004 | Kippenhan, Jr. |
| 7,431,886 | B2 | 10/2008 | Centanni |
| 7,563,329 | B2 | 7/2009 | Lin et al. |
| 9,546,988 | B2 | 1/2017 | Yu |
| 9,603,513 | B2 | 3/2017 | Takada et al. |
| 10,694,930 | B2 | 6/2020 | Iwasaki |
| 2001/0032494 | A1 * | 10/2001 | Greszler ............... A61B 1/125 73/40 |
| 2013/0149690 | A1 | 6/2013 | Schultz |
| 2014/0202497 | A1 | 7/2014 | Kreis et al. |
| 2016/0270645 | A1 | 9/2016 | Akahori |
| 2018/0064325 | A1 | 3/2018 | Onishi et al. |
| 2018/0369876 | A1 | 12/2018 | Olson |

FOREIGN PATENT DOCUMENTS

| CN | 102138568 | 8/2011 |
| EP | 1707222 | 10/2006 |
| EP | 2138127 | 12/2009 |
| WO | 2015/127547 | 9/2015 |

* cited by examiner

*Primary Examiner* — Levon J Shahinian
(74) *Attorney, Agent, or Firm* — Schwegman Lundberg & Woessner, P.A.

(57) ABSTRACT

An apparatus and process to clean medical devices, such as endoscopes, that includes an automatic endoscope reprocessor system equipped with a peracetic acid/hydrogen peroxide sensor are described.

20 Claims, No Drawings

AUTOMATED ENDOSCOPE REPROCESSING UNIT WITH IN-LINE PERACETIC ACID SENSOR

CROSS REFERENCE TO RELATED APPLICATIONS

This application claims priority to and benefit of U.S. Provisional Application with Ser. No. 62/836,906 filed Apr. 22, 2019, entitled AUTOMATED ENDOSCOPE REPROCESSING UNIT WITH IN-LINE PERACETIC ACID SENSOR, which is herein incorporated by reference in its entirety.

FIELD OF THE INVENTION

The invention relates generally to processes to monitor the peracetic acid content of a cleaning solution via a sensor while in use during cleaning of a medical device.

BACKGROUND OF THE INVENTION

Medical devices designed to come into contact with the body of a patient during treatment and or diagnosis require, before being re-used on a new patient, to be "reprocessed", so that the device can be used without concern for patient safety, infection and death resulting from remaining body fluid(s), body waste(s), virus(es) and or bacteria.

Such a sanitation treatment can be a simple disinfection or a sterilization process, performed at either hot or cold temperatures depending on the construction materials of the device.

One approach to clean medical devices which are sensitive to the relatively high temperatures of disinfection autoclaves is by treatment with an aqueous solution that includes one or more chemical agents having decontaminating/sterilant properties. However, such approaches do not ensure that all body fluids and waste have been removed from the surfaces of the medical device. Therefore, cleaning of the medical device often includes a physical cleaning aspect, such as brushing with an instrument, that helps to remove the body fluid(s) and waste(s).

Brushing, rubbing, scraping, scratching, abrading, etc. of the medical device surface, both internal, such as lumens, and external can compromise the surface of the device with scratches or abrasions. Such surface imperfections can be breeding grounds for unwanted and unremoved, debris, body waste, bacteria or virus(es) from the surface of the medical device. Such contamination can serve as a source that can compromise a patient's health and safety. Therefore, it is advantageous to avoid removal of body fluid(s), body waste(s), virus(es) and/or bacteria from medical device surfaces without the use of cleaning materials that have an abrasive aspect to the cleaning.

Therefore, a need exists for disinfection and or sterilization approaches that overcomes one or more of the current disadvantages noted above.

BRIEF SUMMARY OF THE INVENTION

The present invention surprisingly provides a simple and efficient process to clean an interior portion of a medical device, such as a lumen and determine whether the cleaning is sufficient to meet cleanliness standards via a sensor that can monitor the quality/concentration of acetic acid, hydrogen peroxide and/or peracetic acid.

The process disinfects an endoscope comprising the steps of attaching an endoscope to an automated endoscope reprocessing unit. The endoscope has a lumen having a proximal end and a terminal end. The endoscope lumen is treated with a first peracetic acid and hydrogen peroxide solution by passing the peracetic acid and hydrogen peroxide solution through the proximal end of the endoscope through to the terminal end of the endoscope to provide a second peracetic acid and hydrogen peroxide solution.

The second peracetic acid and hydrogen peroxide solution is expelled from the terminal end of the endoscope through the lumen and the expelled peracetic acid and hydrogen peroxide content is measured after treating the lumen to disinfect the endoscope with a sensor capable of measuring peracetic acid or hydrogen peroxide content.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed descriptions are to be regarded as illustrative in nature and not restrictive.

DETAILED DESCRIPTION

In the specification and in the claims, the terms "including" and "comprising" are open-ended terms and should be interpreted to mean "including, but not limited to . . . ." These terms encompass the more restrictive terms "consisting essentially of" and "consisting of."

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", "characterized by" and "having" can be used interchangeably.

Values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" should be interpreted to include not only the explicitly recited amount of about 0.1 wt. % to about 5 wt. %, but also the individual concentrations (e.g., 1%, 2%, 3%, and 4%) and the sub-ranges (e.g., 0.5%, 1.1%, 2.2%, 3.3%, and 4.4%) within the indicated range.

When describing the present invention, the following terms have the following meanings, unless otherwise indicated.

The term "about" can allow for a degree of variability in a value or range, for example, within 10%, within 5%, or within 1% of a stated value or of a stated limit of a range.

As used herein, "cleaner" refers to a substance capable of effectively cleaning a substrate (e.g., medical device). The substance can effectively remove foreign or extraneous matter from the substrate.

As used herein, "solubilizer" refers to a substance that makes soluble, aids in the solubility, or otherwise increases the solubility, of a substance in a liquid diluent or carrier. In specific embodiments of the invention, the solubilizer can include propylene glycol.

As used herein, "diluent" or "carrier" refers to a liquid medium in which substances are suspended, completely dissolved, or partially dissolved in. In specific embodiments of the invention, the diluent can include water (e.g., DI water).

As used herein, "pH" refers to the measure of the acidity or basicity of an aqueous solution. Solutions with a pH less than 7 are said to be acidic and solutions with a pH greater than 7 are basic or alkaline. Pure water has a pH very close to 7. The pH scale is traceable to a set of standard solutions whose pH is established by international agreement. Primary pH standard values are determined using a concentration cell with transference, by measuring the potential difference between a hydrogen electrode and a standard electrode such as the silver chloride electrode. Measurement of pH for aqueous solutions can be done, e.g., with a glass electrode and a pH meter, or using indicators. Mathematically, pH is the negative logarithm of the activity of the (solvated) hydronium ion, more often expressed as the measure of the hydronium ion concentration As used herein, "purified water" refers to water that is mechanically filtered or processed to be cleaned for consumption. Distilled water and deionized (DI) water have been the most common forms of purified water, but water can also be purified by other processes including reverse osmosis, carbon filtration, microfiltration, ultrafiltration, ultraviolet oxidation, or electrodialysis As used herein, "deionized water" or "DI water" refers to demineralized water/DM water (DI water, DIW or de-ionized water), which is water that has had almost all of its mineral ions removed, such as cations like sodium, calcium, iron, and copper, and anions such as chloride and sulfate. Deionization is a chemical process that uses specially manufactured ion-exchange resins which exchange hydrogen ion and hydroxide ion for dissolved minerals, which then recombine to form water. Because most non-particulate water impurities are dissolved salts, deionization produces a high purity water that is generally similar to distilled water, and this process is quick and without scale buildup. However, deionization does not significantly remove uncharged organic molecules, viruses or bacteria, except by incidental trapping in the resin. Specially made strong base anion resins can remove Gram-negative bacteria. Deionization can be done continuously and inexpensively using electrodeionization As used herein, "reversed osmosis water" refers to purified water obtained using a semipermeable membrane. This membrane technology is not properly a filtration method. In reverse osmosis, an applied pressure is used to overcome osmotic pressure, a colligative property, that is driven by chemical potential, a thermodynamic parameter. Reverse osmosis can remove many types of molecules and ions from solutions, and is used in both industrial processes and the production of potable water. The result is that the solute is retained on the pressurized side of the membrane and the pure solvent is allowed to pass to the other side. To be "selective," this membrane should not allow large molecules or ions through the pores (holes), but should allow smaller components of the solution (such as the solvent) to pass freely.

As used herein, "tap water" or "running water," "city water," or "municipal water" refers to water supplied to a tap (valve). Its uses include drinking, washing, cooking, and the flushing of toilets. Indoor tap water is distributed through "indoor plumbing", which has existed since antiquity but was available to very few people until the second half of the 19th century, when it began to propagate in what are now the developed countries. It became common in many regions during the 20th century, and is now lacking only among the poor, especially in developing countries. Calling a water supply "tap water" distinguishes it from the other main types of fresh water which may be available; these include water from rainwater-collecting cisterns, water from village pumps or town pumps, or water carried from streams, rivers, or lakes (whose potability may vary).

As used herein, "medical device" refers to an instrument, apparatus, implant, in vitro reagent, or similar or related article that is used to diagnose, prevent, or treat disease or other conditions, and does not achieve its purposes through chemical action within or on the body (which would make it a drug). Whereas medicinal products (also called pharmaceuticals) achieve their principal action by pharmacological, metabolic or immunological means, medical devices act by other means like physical, mechanical, or thermal means. Medical devices vary greatly in complexity and application. Examples range from simple devices such as tongue depressors, medical thermometers, and disposable gloves to advanced devices such as computers which assist in the conduct of medical testing, implants, and prostheses. The design of medical devices constitutes a major segment of the field of biomedical engineering. In specific embodiments, the medical device can include an endoscope (e.g., flexible endoscope).

As used herein, "endoscope" refers to an instrument used to examine the interior of a hollow organ or cavity of the body. Unlike most other medical imaging devices, endoscopes are inserted directly into the organ. Endoscope can also refer to using a borescope in technical situations where direct line of-sight observation is not feasible.

An endoscope can consist of: (a) a rigid or flexible tube; (b) a light delivery system to illuminate the organ or object under inspection. The light source is normally outside the body and the light is typically directed via an optical fiber system; (c) a lens system transmitting the image from the objective lens to the viewer, typically a relay lens system in the case of rigid endoscopes or a bundle of fiberoptics in the case of a fiberscope; (d) an eyepiece. Modern instruments may be videoscopes, with no eyepiece, a camera transmits image to a screen for image capture; and (e) an additional channel to allow entry of medical instruments or manipulators.

As used herein, "flexible endoscope" refers to an endoscope that includes a flexible tube.

As used herein, "automatic endoscope reprocessor" or refers to an apparatus employed to wash a medical device, such as a flexible endoscope or colonoscope. Such an apparatus or machine can also disinfect the medical device, as well as optionally dry and optionally store the medical device. Suitable apparatus or machines that can wash and disinfect the medical device include, e.g., ADVANTAGE PLUS Pass-Thru Automated Endoscope Reprocessor, MEDIVATORS Advantage Plus Endoscope Reprocessing System, CER Optima AER, RapidAER Endscope Reprocessor, CER Series Reprocessors, Medivators DSD Edge Dual Basin AER, Medivators DSD-2011LT Dual Basin AER or Medivators SSD-102LT Single Basin AER, all manufactured by Medivators/Cantel.

For example, a method for cleaning and disinfection or sterilization of endoscopes employs an automated endoscope reprocessor ("AER") which both washes and then disinfects or sterilizes the endoscope. Typically such a unit comprises a basin with a selectively opened and closed cover member to provide access to the basin. Pumps connect to various channels (lumen) through the endoscope to flow fluid there through and an additional pump flows fluid over the exterior surfaces of the endoscope contained in the basin.

Typically, a detergent washing cycle is followed by rinsing and then a sterilization or disinfection cycle and rinse.

The AER can have various ports about the basin to drain the cleaning solution or to serve as a port to monitor the acceptability of the cleaning solution via a sensor. Alternatively, the sensor can be embedded directly into the basin and/or can be connected directly to a terminal portion of a lumen of the endoscope contained within the basin.

As used herein, "clean," "cleaning," "wash," or "washing" refers to the process of freeing a substrate from foreign or extraneous matter; the process of removing foreign or extraneous matter from a substrate (e.g., medical device).

As used herein, "disinfect" or "disinfecting" refers to the process of destroying, removing, killing and/or inhibiting the action of microorganisms located on a substrate (e.g., medical device).

As used herein, "dry" or "drying" refers to the process of removing moisture from a substrate (e.g., medical device). The process can be carried out, e.g., employing heat (elevated temperature).

As used herein, "store" or "storing" refers to the process of housing a substrate (e.g., medical device) for future use.

This invention relates to a method for conditioning medical equipment following processing (cleaning and disinfection) of said equipment, and to apparatus for use in such a method. In particular, the invention relates to a method and apparatus for conditioning a flexible medical endoscope, following processing of said endoscope to a state of high level disinfection.

The term "disinfection" is used herein in preference to the term "sterility" since the latter implies the complete absence of pathogenic organisms, which in practice is rarely, if ever, achievable. It is to be appreciated however that the ultimate aim of disinfecting medical equipment is indeed to get as close to absolute sterility as is practicable. The term "conditioning" is used herein to refer to a method of maintaining the disinfection of medical equipment following processing thereof to a state of high level disinfection.

The present invention has been developed in connection with the processing and storage of flexible medical endoscopes, and therefore will be described herein with particular emphasis on this application. It is envisaged however, that the method of the present invention may be applied to the processing and storage of substantially all types of medical, surgical, dental and veterinary equipment, apparatus, and instruments, especially those with lumens.

After use in an endoscopic procedure, flexible medical endoscopes are usually subjected to "processing", consisting of rigorous manual cleaning followed by placing the endoscope in an Automated Endoscope Re-processor (AER) which effects a further cleaning and disinfecting procedure to bring the endoscope to a High Level Disinfection Status (HLDS). The endoscope is then stored in a clean environment. Under normal storage conditions, the degree of disinfection of the endoscope can only be maintained at an acceptable level for a relatively short period, usually about 3 hours. This is due to the multiplication of residual pathogens which may remain on the endoscope after disinfection, or which may be present in the atmosphere. If the endoscope is not used in a further endoscopic procedure within this time, then further processing will be necessary prior to its next use. Frequent and repeated processing is undesirable, since it reduces the availability of the endoscope for endoscopic procedures, while increasing the operating costs, due to the need for cleaning and disinfectant materials and the operation of cleaning equipment. Furthermore, repeated processing reduces the lifetime of the endoscope due to wear and tear.

The loss of HLDS over the 3 hour storage period is due to the inability of the AER completely to dry the internal channels of the endoscope, due to the small internal diameter of these channels. The residual moisture within the channels provides an environment in which micro-organisms can quickly multiply.

The term "cleaning composition" refers to a substance that when applied to non-living objects, effectively removes foreign matter located on the objects. For example, when used to clean medical devices, such as flexible endoscopes, the cleaning solution(s) described herein can effectively remove from the medical device at least one of soil, blood, protein, carbohydrate, bodily fluid, and fecal matter.

The term "room temperature" as used herein refers to a temperature of about 15° C. to 28° C.

The term "hydrogen peroxide" or "$H_2O_2$" refers to the compound chemically designated as dihydrogen dioxide, having the CAS Reg. No. 7722-84-1. In specific embodiments of the invention, the hydrogen peroxide includes water. In further specific embodiments of the invention, the hydrogen peroxide is 50% wt. % hydrogen peroxide in water. The hydrogen peroxide can be present in the composition, in any suitable and effective amount.

The term "organic acid" refers to an organic compound with acidic properties. The most common organic acids are the carboxylic acids, whose acidity is associated with their carboxyl group —COOH. Sulfonic acids, containing the group —$SO_2OH$, are relatively stronger acids. The relative stability of the conjugate base of the acid determines its acidity. Other groups can also confer acidity, usually weakly: —OH, —SH, the enol group, and the phenol group. Organic compounds containing these groups are generally referred to as organic acids. An example of an organic acid is acetic acid.

The term "acetic acid" or "ethanoic acid" refers to an organic compound with the chemical formula $CH_3CO_2H$ (also written as $CH_3COOH$), having the CAS Reg. No. 64-19-7.

The term "glacial acetic acid" refers to undiluted and relatively concentrated, water-free (anhydrous) acetic acid.

The term "peracetic acid," "peroxyacetic acid," or "PAA" refers to an organic compound with the chemical formula $CH_3CO_3H$.

The term "chelator," "chelant" or "chelating agent" refers to a compound that forms soluble, complex molecules with certain metal ions, inactivating the metal ions (or to some extent, countering the effects of the metal ions), so that they cannot normally react with other compounds, elements or ions. In specific embodiments, the chelator effectively chelates transition metals. One suitable type of chelator is/are sulfonic acids, more particularly, polymers or solid supports which contain sulfonic acid functionality. In specific embodiments, the chelator will effectively chelate any transition metals and/or alkaline earth metals present in any of the components of the composition.

In particular, the chelator can be a sulfonic acid group that is incorporated into a polymer. For example, the polymer can be styrene based that is functionalized with sulfonic acid groups. The styrenic polymer can be a copolymer, such as styrene/divinylbenzene. The polymer may further be cross-linked. Examples of commercially available sulfonic acid functionalized polymers include those such as Dowex® 50WX4-200, Dowex® DR2030, Amberlite IR120 Na, Amberlite IRN99, Amberlyst 15 hydrogen (CAS Number 39389-20-3) and Amberlite strong acidic cation exchange sodium form available from Dow Chemical Company, which are styrene-divinylbenzene copolymers.

Alternatively, a copolymer of tetrafluoroethylene (TFE) and Sulfonyl Fluoride Vinyl Ether (SFVE) $F_2C=CF-O-CF_2CF_2-SO_2F$ is a useful material. Aquivion® PFSA (perfluorosulfonic acid) ionomers, available from Solvay, are based on this copolymer and are available in a membrane, as a powder, in a dispersion or as pellets.

In one aspect, the perfluorosulfonic acid pellets can be extruded/coextruded with other polymers to form films or shaped into a container to hold the remaining components of the embodiments. Suitable extrusion polymers include, for example, polyethylenes and polypropylenes.

In another embodiment, the polymer can be derived from 2-acrylamido-2-methylpropane sulfonic acid (AMPS). Additionally, AMPS can be used to coat the lining of a container and then be polymerized to the surface of the container as a protective/chelating coating.

It should be understood that the requisite sulfonic acid group may need to be first treated with an acidic solution to provide the free acid as necessary.

The polymeric resin chelator can be added to the compositions described herein. Alternatively, the compositions can be passed through the polymeric resin chelator. In another embodiment, the polymeric resin chelator can be in the form of a membrane and the membrane is in contact and remains in contact with the composition. In still another embodiment, the polymeric resin chelator is incorporated into a container which hold the compositions described herein. In certain embodiments, the polymer resin chelator is coated onto the interior of a container that is used to store the compositions described herein. In still another embodiment, the polymeric chelator can be placed within a "mesh pouch" or other containment system that can be placed into a container with the compositions described herein.

One advantage of utilizing the polymeric resin chelator is that users of the compositions often contaminate the composition in between uses. That is, an individual may place a used wipe, sponge, or rag, medical device, instrument, etc. against or within the container that houses the composition, thus transferring contaminants to the container. The polymeric resin chelators described herein help to stabilize the peracetic acid/hydrogen peroxide compositions by complexing with/removing the undesired contaminants, such as metal ions.

It should be understood that one advantage of the polymeric resin chelator is that it does not dissolve in the embodiments described herein. That is, the polymer resin remains in the solution but does not become homogeneous with the remaining components. Not to be limited by theory, it is believed that the polymeric resin chelator provides surface contact with the components of the composition and removes metallic contaminants from the solution to stabilize the composition. As a result, the components of the composition, e.g., the hydrogen peroxide and/or the peracetic acid, do not degrade over time due to metallic components. Additionally, the polymeric resin chelator does not cause a residue to remain on a treated surface after the surface has been treated with the compositions described herein.

The term "anticorrosive agent" or "corrosion inhibitor" refers to a compound that, when added to a liquid or gas, decreases the corrosion rate of a material, typically a metal or an alloy. Suitable anticorrosive agents include, e.g., benzotriazole and sodium dodecyl sulfate (SDS).

The term "benzotriazole" or "BTA" refers to the compound 1H-benzotriazole or 1,2,3-benzotriazole, having the CAS Reg. No. 95-14-7.

The term "surfactant" refers to a compound capable of lowering the surface tension of a liquid, the interfacial tension between two liquids, or that between a liquid and a solid. Surfactants may act as detergents, wetting agents, emulsifiers, foaming agents, and/or dispersants. The surfactant can be non-ionic, anionic or cationic. Additionally, the surfactant can include one or more non-ionic surfactants, one or more anionic surfactants, and/or one or more cationic surfactants.

The term "non-ionic surfactant" or "nonionic surfactant" refers to a surfactant, in which the total number of electrons is equal to the total number of protons, giving it a net neutral or zero electrical charge. One suitable class of non-ionic surfactants includes the Pluronic® poloxamers.

Poloxamers are nonionic triblock copolymers composed of a central hydrophobic chain of polyoxypropylene (poly (propylene oxide)) flanked by two hydrophilic chains of polyoxyethylene (poly(ethylene oxide)). Poloxamers are also known by the trade name Pluronics®.

Because the lengths of the polymer blocks can be customized, many different poloxamers exist, that have slightly different properties. For the generic term "poloxamer," these copolymers are commonly named with the letter "P" (for poloxamer) followed by three digits, the first two digits "x" (times) 100 give the approximate molecular mass of the polyoxypropylene core, and the last digit×10 gives the percentage polyoxyethylene content (e.g., P407=Poloxamer with a polyoxypropylene molecular mass of 4,000 g/mol and a 70% polyoxyethylene content). For the Pluronic® tradename, coding of these copolymers starts with a letter to define its physical form at room temperature (L=liquid, P=paste, F=flake (solid)) followed by two or three digits. The first digit (two digits in a three-digit number) in the numerical designation, multiplied by 300, indicates the approximate molecular weight of the hydrophobe; and the last digit×10 gives the percentage polyoxyethylene content (e.g., L61=Pluronic with a polyoxypropylene molecular mass of 1,800 g/mol and a 10% polyoxyethylene content). In the example given, poloxamer 181 (P181)=Pluronic L61.

The term "Pluronic® 10R5 surfactant block copolymer" refers to polyoxypropylene-polyoxyethylene block copolymer, having the CAS Reg. No. 9003-11-6.

Other nonionic surfactants include, but are not limited to, fatty alcohols, polyoxyethylene glycol alkyl ethers (Brij), polyoxypropylene glycol alkyl ethers, glucoside alkyl ethers, polyoxyethylene glycol octylphenol ethers, polyoxyethylene glycol alkylphenol ethers, glycerol alkyl esters, polyoxyethylene glycol sorbitan alkyl esters, sorbitan alkyl esters, cocamide MEAs, cocamide DEAs, dodecyl dimethylamine oxides, block copolymers of polyethylene glycol and polypropylene glycols.

Suitable fatty alcohols include, but are not limited to, cetyl alcohol, stearyl alcohol, cetostearyl alcohol (consisting predominantly of cetyl and stearyl alcohols) and oleyl alcohol.

Suitable polyoxyethylene glycol alkyl ethers, include but are not limited to (Brij), for example $CH_3-(CH_2)_{10-16}-(O-C_2H_4)_{1-25}-OH$, or octaethylene glycol monododecyl ether or pentaethylene glycol monododecyl ether.

Suitable polyoxypropylene glycol alkyl ethers include $CH_3-(CH_2)_{10-16}-(O-C_3H_6)_{1-25}-OH$.

Suitable glucoside alkyl ethers include $CH_3$—$(CH_2)_{10-16}$—(O-Glucoside)$_{1-3}$-OH, and, for example, include decyl glucoside, lauryl glucoside, and octyl glucoside.

Suitable polyoxyethylene glycol octylphenol ethers include $C_8H_{17}$—$(C_6H_4)$—$(O$—$C_2H_4)_{1-25}$—OH. One exemplary material is TRITON X-100.

Suitable polyoxyethylene glycol alkylphenol ethers include $C_9H_{19}$—$(C_6H_4)$—$(O$—$C_2H_4)_{1-25}$—OH. One example is Nonoxynol-9.

In one aspect, a suitable glycerol alkyl ester is glyceryl laurate.

In another aspect, a suitable polyoxyethylene glycol sorbitan alkyl ester is polysorbate.

In still another aspect, suitable sorbitan alkyl esters are referred to as SPAN, e.g., SPAN-20, sorbitan monolaurate.

The term "cationic surfactant" refers to a surfactant, in which the total number of electrons is less than the total number of protons, giving it a net positive electrical charge.

One kind of cationic surfactant is typically based on pH-dependent primary, secondary or tertiary amines. The primary amines become positively charged at a pH<10, and the secondary amines become charged at a pH<4. One example is octenidine dihydrochloride.

Another type of cationic surfactant is based on permanently charged quaternary ammonium cations, such as alkyltrimethylammonium salts. These include but are not limited to cetyl trimethylammonium bromide (CTAB), hexadecyl trimethyl ammonium bromide, cetyl trimethylammonium chloride (CTAC), cetylpyridinium chloride (CPC), polyethoxylated tallow amine (POEA), benzalkonium chloride (BAC), benzethonium chloride (BZT), 5-Bromo-5-nitro-1,3-dioxane, dimethyldioctadecylammonium chloride and dioctadecyldimethylammonium bromide (DODAB).

The term "anionic surfactant" refers to a surfactant in which the total number of electrons is greater than the total number of protons, giving it a net negative electrical charge. One suitable anionic surfactant is sodium lauryl sulfate.

Anionic surfactants have a permanent anion, such as a sulfate, sulfonate or phosphate anion associated with the surfactant or has a pH-dependent anion, for example, a carboxylate.

Sulfates can be alkyl sulfate or alkyl ether sulfates.

Suitable alkyl sulfates include, but are not limited to, ammonium lauryl sulfate or sodium lauryl sulfate (SDS). Suitable alkyl ether sulfates include, but are not limited to, sodium laureth sulfate, also known as sodium lauryl ether sulfate (SLES) or sodium myreth sulfate.

Suitable sulfonates include, but are not limited to, docusate (dioctyl sodium sulfosuccinate), fluorosurfactants that are sulfonated and alkyl benzene sulfonates.

Typical sulfonated fluorosurfactants include, but are not limited to, perfluorooctanesulfonate (PFOS) or perfluorobutanesulfonate.

Phosphates are typically alkyl aryl ether phosphates or alkyl ether phosphates.

Carboxylates are typically alkyl carboxylates, such as fatty acid salts (soaps), such as for example, sodium stearate. Alternatively, the carboxylate can be, but is not limited to, sodium lauryl sarcosinate. In another alternative aspect, the carboxylate includes but is not limited to a carboxylated fluorosurfactant, such as perfluorononanoate, or perfluorooctanoate (PFOA or PFO).

When a single surfactant molecule exhibits both anionic and cationic dissociations it is called amphoteric or zwitterionic. Zwitterionic (amphoteric) surfactant is based on primary, secondary or tertiary amines or quaternary ammonium cation also having a sulfonate, carboxylate or a phosphate.

Suitable zwitterionic surfactants include, but are not limited to, CHAPS (3-[(3-Cholamidopropyl)dimethylammonio]-1-propanesulfonate) or a sultaine. The sultaine is typically cocamidopropyl hydroxysultaine.

In one aspect, the carboxylate cation is an amino acid, imino acid or betaine. In one aspect, the betaine is typically cocamidopropyl betaine.

When the zwitterionic surfactant includes a phosphate, lecithin is often chosen as the counterion.

The term "sodium dodecyl sulfate," "SDS," "NaDS," "sodium lauryl sulfate," or "SLS" refers to an organic compound with the formula $CH_3(CH_2)_{11}OSO_3Na$), having the CAS Reg. No. 151-21-3.

The term "disinfectant" refers to a substance that when applied to non-living objects, destroys microorganisms that are living on the objects. The term "disinfect" refers to the process of destruction or prevention of biological contaminants. Disinfection does not necessarily kill all microorganisms, especially nonresistant bacterial spores; it is less effective than sterilization, which is an extreme physical and/or chemical process that kills all types of life.

Disinfectants are different from other antimicrobial agents such as antibiotics, which destroy microorganisms within the body, and antiseptics, which destroy microorganisms on living tissue. Disinfectants are also different from biocides. The latter are intended to destroy all forms of life, not just microorganisms. Sanitizers are substances that simultaneously clean and disinfect.

The term "CFU" refers colony forming units and is a measure of viable cells in which a colony represents an aggregate of cells derived from a single progenitor cell.

In various embodiments, the composition includes: (a) hydrogen peroxide; (b) an organic acid; (c) a chelator that is not Dequest® 2010 (1-hydroxyethylidene-1,1,-diphosphonic acid), in particular a sulfonic acid containing polymer, copolymer or a support functionalized with sulfonic acid groups; and (d) surfactant.

It should be understood that certain embodiments disclosed herein do not include 1-hydroxyethylidene-1,1,-diphosphonic acid. In embodiments disclosed herein, the compositions and methods do not leave a residue on a treated surface after use of the composition to treat the surface.

In another aspect, (1-hydroxyethylidene-1,1,-diphosphonic acid) can be included in the cleaning composition.

The use of the polymeric stabilizer is detailed in pending PCT application PCT/US19/53090, filed Sep. 26, 2019, entitled "Peracetic Acid Stabilized Compositions with Polymeric Resins Chelators", the contents of which are incorporated herein by reference.

It is appreciated that those of ordinary skill in the art fully understand and appreciate that when a composition includes more than one component, the composition may also include additional components formed as a product of the reaction between the components in the composition. For example, those of skill in the art fully understand and appreciate that a composition including hydrogen peroxide ($H_2O_2$) and acetic acid ($CH_3CO_2H$) also includes the oxidized product of acetic acid, peracetic acid ($CH_3CO_3H$). As such, reference to the composition including hydrogen peroxide ($H_2O_2$) and acetic acid ($CH_3CO_2H$) is proper, as well as reference to the composition being formed from hydrogen peroxide ($H_2O_2$) and acetic acid ($CH_3CO_2H$). To that end, a composition of acetic acid and hydrogen peroxide will include significant and appreciable amounts of peracetic acid formed from the reaction of acetic acid with hydrogen peroxide. Further, it is appreciated that those of ordinary skill in the art fully understand and appreciate that an equilibrium exists between hydrogen peroxide and acetic acid, and peracetic acid.

In various embodiments, peracetic acid is present in about 1 wt. % to about 15 wt. % of the composition. In some embodiments, peracetic acid is present in about 2-14 wt. %, 3-12 wt. %, 4-11 wt. %, 5-9 wt. %, about 6-8 wt. %, or about 1 wt. %, 2 wt. %, 3 wt. %, 4 wt. %, 5 wt. %, 6 wt. %, 7 wt. %, 8 wt. %, 9 wt. %, 10 wt. %, 11 wt. %, 12 wt. %, 13 wt. %, 14 wt. %, or about 15 wt. % or more of the composition. In some embodiments, peracetic acid is present in about 5 wt. % to about 7.5 wt. % of the composition.

In various embodiments, hydrogen peroxide is present in about 10 wt. % to about 50 wt. % of the composition. In some embodiments (e.g., before equilibration and formation of PAA), the hydrogen peroxide is present in about 15-45 wt. %, 20-35 wt. %, or about 25-30 wt. % of the composition. In some embodiments (e.g., after equilibration and formation of PAA), the hydrogen peroxide is present in about 10-40 wt. %, 15-35 wt. %, 18-30 wt. % or about 20-26 wt. % of the composition. In some embodiments, the hydrogen peroxide is present in about 16 wt. %, 18 wt. %, 20 wt. %, 21 wt. %, 22 wt. %, 23 wt. %, 24 wt. %, 25 wt. %, 26 wt. %, 27 wt. %, 28 wt. %, 29 wt. %, 30 wt. %, 31 wt. %, 32 wt. %, 34 wt. %, or about 36 wt. %. In some embodiments, the hydrogen peroxide is about 35 wt. % in water, present in about 18 wt. % to about 32 wt. % of the composition. In some embodiments, hydrogen peroxide is about 35 wt. % in water, present in about 28 wt. % of the composition. In some embodiments, hydrogen peroxide is about 35 wt. % in water, present in about 20 wt. % to about 26 wt. % of the composition.

In various embodiments, the organic acid includes acetic acid. In some embodiments, the organic acid comprises glacial acetic acid. In some embodiments, the organic acid includes acetic acid, present in at least about 3 wt. % of the composition. In some embodiments (e.g., before equilibration and formation of PAA), the organic acid includes acetic acid, present in about 1-50 wt. %, 2-45 wt. %, 3-40 wt. %, 4-35 wt. %, 6-30 wt. %, 8-24 wt. %, 10-22 wt. %, 12-20 wt. %, about 14-18 wt. %, or about 4 wt. %, 5 wt. %, 6 wt. %, 7 wt. %, 8 wt. %, 9 wt. %, 10 wt. %, 11 wt. %, 12 wt. %, 13 wt. %, 14 wt. %, 15 wt. %, 16 wt. %, 17 wt. %, 18 wt. %, 19 wt. %, 20 wt. %, 21 wt. %, 22 wt. %, 23 wt. %, 24 wt. %, or about 25 wt. % of the composition. In some embodiments (e.g., after equilibration and formation of PAA), the organic acid includes acetic acid, present in about 1-20 wt. %, 2-18 wt. %, 3-17 wt. %, 4-16 wt. %, 5-15 wt. %, 6-14 wt. %, 7-13 wt. %, 8-12 wt. %, or about 9-11 wt. % of the composition. In some embodiments, the organic acid includes acetic acid, present in about 9 wt. % to about 11 wt. % of the composition. In some embodiments, the organic acid comprises acetic acid, present in about 16 wt. % of the composition.

In various embodiments, the chelator effectively chelates transition metals. In some embodiments the chelator includes a polymeric sulfonic acid resin.

In various embodiments, the surfactant includes a non-ionic surfactant. In various embodiments, the surfactant includes at least one of an anionic and cationic surfactant. In some embodiments the surfactant includes Pluronic® 10R5 surfactant block copolymer. In some embodiments the surfactant includes Pluronic® 10R5 surfactant block copolymer, present in at least about 0.1 wt. % of the composition.

In some embodiments, the surfactant includes Pluronic® 10R5 surfactant block copolymer, present in about 0.1-8.0 wt. %, 0.3-7.0 wt. %, 0.5-6.0 wt. %, 0.7-5.0 wt. %, 0.8-4.0 wt. %, about 1.0-3.0 wt. %, or about 0.5 wt. %, 1.0 wt. %, 1.4 wt. %, 1.8 wt. %, 2.0 wt. %, 2.2 wt. %, 2.6 wt. %, or about 3.0 wt. % of the composition. In some embodiments, the surfactant includes Pluronic® 10R5 surfactant block copolymer, present in about 2 wt. % of the composition.

In various embodiments, the composition includes about 28 wt. % hydrogen peroxide, about 16 wt. % acetic acid, about 0.2 wt. % to about 2 wt. % polymeric resin chelator, optionally, about 2.0 wt. % Pluronic® 10R5 surfactant block copolymer, and about 53 wt. % deionized water.

In various embodiments, the composition includes about 20.0 to about 26.0 wt. % hydrogen peroxide, about 9.0 to about 11.0 wt. % acetic acid, about 0.2 wt. % to about 2 wt. % polymeric resin chelator, optionally, about 2.0 wt. % Pluronic® 10R5 surfactant block copolymer, about 53 wt. % deionized water and about 6.8 to about 7.5 wt. % peracetic acid.

In specific embodiments, the cleaning solution(s) described herein can be formulated as, can exist as, and can be commercially available as a liquid concentrate disinfectant. The term "liquid concentrate" refers to a composition that is relatively undiluted and concentrated, having a low content of carrier, e.g., water. Having the composition be commercially available as a liquid concentrate will typically save costs associated with the manufacturing, shipping, and/or storage of the product.

When the cleaning solution(s) described herein is formulated as a liquid concentrate, the concentrate can subsequently be diluted with an appropriate amount of carrier (e.g., water) prior to use. Additionally, although considered to be a concentrate, when the cleaning solution(s) described herein is formulated as a liquid concentrate, a discrete and finite amount of carrier (e.g., water) can be employed.

In various embodiments, the present invention provides for a one part, liquid concentrate disinfectant including about 20.0 about 26.0 wt. % hydrogen peroxide, about 9.0 to about 11.0 wt. % acetic acid, about 0.2 wt. % to about 2 wt. % polymeric resin chelator, about 2.0 wt. % Pluronic® 10R5 surfactant block copolymer, about 53 wt. % deionized water and about 6.8 to about 7.5 wt. % peracetic acid.

In various embodiments, the cleaning solution(s) described herein can be configured for use in contacting at least one of medical equipment, medical device (e.g., reusable medical device or instrument, such as an endoscope), surface in the medical industry, dental equipment, dental device, and surface in the dental industry. In some embodiments, the cleaning solution(s) described herein may be used in the reconditioning of a soiled endoscopic device. In some embodiments, the compositions of the invention are useful during the disinfection step of the high level disinfection cleaning process following use of the endoscope in a medical procedure. The term "endoscopic device" includes a plurality of minimally invasive surgical devices (e.g., scopes) that have been developed for specific uses. For example, upper and lower endoscopes are utilized for accessing the esophagus/stomach and the colon, respectively, angioscopes are utilized for examining blood vessels, and laparoscopes are utilized for examining the peritoneal cavity.

In some embodiments, catalysts for the formation of peracetic acid from hydrogen peroxide and acetic acid are employed. Suitable catalysts include, for example, inorganic acids, such as sulfuric acid ($H_2SO_4$), hydrochloric acid (HCl), phosphoric acid ($H_3PO_4$), and nitric acid ($HNO_3$).

In specific embodiments, the cleaning solution(s) described herein can be non-corrosive. The term "non-corrosive" or "noncorrosive" refers to a substance that will not destroy or irreversibly damage another surface or substance with which it comes into contact. The main hazards to people include damage to the eyes, the skin, and the tissue under the skin; inhalation or ingestion of a corrosive substance can damage the respiratory and gastrointestinal tracts. Exposure results in chemical burn. Having the composition be relatively non-corrosive will allow the user to employ the composition over a wider range of uses, exposing the composition to a wider range of substrates. For example, having the composition be relatively non-corrosive will allow the user to employ the composition as a disinfectant with certain medical devices that are highly sensitive to corrosive substances.

In specific embodiments, the cleaning solution(s) described herein can be non-toxic. The term "non-toxic" refers to a substance that has a relatively low degree to which it can damage a living or non-living organism. Toxicity can refer to the effect on a whole organism, such as an animal, bacterium, or plant, as well as the effect on a substructure of the organism, such as a cell (cytotoxicity) or an organ (organotoxicity), such as the liver (hepatotoxicity). A central concept of toxicology is that effects are dose-dependent; even water can lead to water intoxication when taken in large enough doses, whereas for even a very toxic substance such as snake venom there is a dose below which there is no detectable toxic effect. Having the composition be relatively non-toxic will allow a wider range of users be able to safely handle the composition, without serious safety concerns or risks.

In specific embodiments, the cleaning solution(s) described herein can be stable over extended periods of time (i.e., has a long-term stability). The term "long-term stability" refers to a substance undergoing little or no physical and/or chemical decomposition or degradation, over extended periods of time.

In further specific embodiments, the cleaning solution(s) described herein can be stable over extended periods of time, such that at about 1 atm and about 19° C., less than about 20 wt. %, e.g., 15 wt. %, 10 wt. %, or 5 wt. %, of each component independently degrades over about one year. In additional specific embodiments, the cleaning solution(s) described herein can be stable over extended periods of time, such that at about 1 atm and about 19° C., at least about 80 wt. % of each component, e.g., 85 wt. %, 90 wt. %, 95 wt. %, is independently present after about one year.

Having the composition be relatively stable over extended periods of time will allow the composition to retain its effectiveness over that time, ensuring that it will remain useful and active for its intended purpose. In contrast, in those compositions that do not retain their effectiveness over that time, product loss can result, which can be financially costly. Additionally, risks associated with the use of a product that has lost some or all of its effectiveness for the intended purpose can be hazardous, in that the product may not effectively achieve the desired goal. For example, when used to disinfect a medical device, use of a composition that has lost some or all of its effectiveness as a disinfectant may not effectively disinfect the medical device. Medical injuries can be sustained by the patient, including serious infections.

In specific embodiments, the cleaning solution(s) described herein can be formulated as, can exist as, and is commercially available as, a one-part composition. The term "one-part composition" refers to all chemical components of a composition being present together, such that they are each in intimate and physical contact with one another, and are each present in a single container. Having the composition be commercially available as a one-part composition will be more cost effective (e.g., lower manufacturing costs associated with fewer containers), and will avoid the necessity of the user mixing or combining multiple components together, prior to using.

In specific embodiments, the cleaning solution(s) described herein can be essentially free of buffer. In further specific embodiments, the cleaning solution(s) described herein can include less than about 0.1 wt. % buffer. The term "buffer," "buffering agent," or "buffering substance" refers to a weak acid or base used to maintain the acidity (pH) of a solution at a chosen value. The function of a buffering agent is to prevent a rapid change in pH when acids or bases are added to the solution. Buffering agents have variable properties—some are more soluble than others; some are acidic while others are basic.

In specific embodiments, the cleaning solution(s) described herein can be essentially free of transition metals. In further specific embodiments, the cleaning solution(s) described herein can include less than about 0.001 wt. % transition metals. In further specific embodiments, the cleaning solution(s) described herein can include less than about 0.0001 wt. % transition metals. In further specific embodiments, the cleaning solution(s) described herein can include less than about 0.00001 wt. % transition metals. Having the composition include a minimal amount of transition metals decreases the likelihood that the transition metals will cause degradation and/or decomposition of the composition, over the extended periods of time associates with the manufacturing, shipping, and storage of the composition. This is especially so when the composition is formulated as a concentrated, one-part composition.

The term "transition metal," "transition metals" or "transition element" refers to an element whose atom has an incomplete d sub-shell, or which can give rise to cations with an incomplete d sub-shell. Transition metals include scandium (Sc), titanium (Ti), vanadium (V), chromium (Cr), manganese (Mn), iron (Fe), cobalt (Co), nickel (Ni), copper (Cu), zinc (Zn), yttrium (Y), zirconium (Zr), niobium (Nb), molybdenum (Mo), technetium (Tc), ruthenium (Ru), rhodium (Rh), palladium (Pd), silver (Ag), cadmium (Cd), hafnium (Hf), tantalum (Ta), tungsten (W), rhenium (Re), osmium (Os), iridium (Ir), platinum (Pt), gold (Au), mercury (Hg), rutherfordium (Rf), dubnium (db), seaborgium (Sg), bohrium (Bh), hassium (Hs) and copernicium (Cn).

In specific embodiments of the invention, the transition metal can be naturally occurring. Naturally occurring transition metals include scandium (Sc), titanium (Ti), vanadium (V), chromium (Cr), manganese (Mn), iron (Fe), cobalt (Co), nickel (Ni), copper (Cu), zinc (Zn), yttrium (Y), zirconium (Zr), niobium (Nb), molybdenum (Mo), technetium (Tc), ruthenium (Ru), rhodium (Rh), palladium (Pd), silver (Ag), cadmium (Cd), hafnium (Hf), tantalum (Ta), tungsten (W), rhenium (Re), osmium (Os), iridium (Ir), platinum (Pt), gold (Au), and mercury (Hg).

In specific embodiments, the cleaning solution(s) described herein can be essentially free of heavy metals. In further specific embodiments, the cleaning solution(s) described herein can include less than about 0.001 wt. % heavy metals. In further specific embodiments, the cleaning solution(s) described herein can include less than about 0.0001 wt. % heavy metals. In further specific embodiments, the cleaning solution(s) described herein can include less than about 0.00001 wt. % heavy metals. Having the composition include a minimal amount of heavy metals decreases the likelihood that the transition metals will cause degradation and/or decomposition of the composition, over the extended periods of time associates with the manufacturing, shipping, and storage of the composition. This is especially so when the composition is formulated as a concentrated, one-part composition.

The term "heavy metal," "heavy metals" or "toxic metal" refers to metals that are relatively toxic, and mainly include the transition metals, some metalloids, lanthanides, and actinides. Examples of toxic metals include, e.g., iron (Fe), cobalt (Co), copper (Cu), manganese (Mn), molybdenum (Mo), zinc (Zn), mercury (Hg), plutonium (Pu), lead (Pb), vanadium (V), tungsten (W), cadmium (Cd), aluminium (Al), beryllium (Be), and arsenic (As).

The present invention also provides for a kit that includes: (a) an enclosed container that includes a removable closure; (b) the cleaning solution(s) described herein as described herein, which is located inside the enclosed container; and (c) printed indicia located on the enclosed container.

In specific embodiments, the enclosed container can be opaque. In additional specific embodiments, the enclosed container can be manufactured from high density polyethylene (HDPE), thereby providing the requisite opacity. Having the enclosed container be manufactured from high density polyethylene (HDPE) will decrease the likelihood that the composition will degrade and/or decompose over extended periods of time, due to excessive exposure to direct sunlight.

The term "high-density polyethylene" or "HDPE" refers to a polyethylene thermoplastic made from petroleum. The mass density of high-density polyethylene can range from 0.93 to 0.97 g/cm$^3$. Although the density of HDPE is only marginally higher than that of low-density polyethylene, HDPE has little branching, giving it stronger intermolecular forces and tensile strength than LDPE. The difference in strength exceeds the difference in density, giving HDPE a higher specific strength. It is also harder and more opaque and can withstand somewhat higher temperatures (120° C./248° F. for short periods, 110° C./230° F. continuously). HDPE is resistant to many different solvents.

The term "solvent" as used herein refers to a liquid that can dissolve a solid, liquid, or gas. Non-limiting examples of solvents are silicones, organic compounds, water, alcohols, ionic liquids, and supercritical fluids.

The term "opaque" refers to an object that is neither transparent (allowing all light to pass through) nor translucent (allowing some light to pass through). When light strikes an interface between two substances, in general some may be reflected, some absorbed, some scattered, and the rest transmitted (also see refraction). Reflection can be diffuse, for example light reflecting off a white wall, or specular, for example light reflecting off a mirror. An opaque substance transmits no light, and therefore reflects, scatters, or absorbs all of it. Both mirrors and carbon black are opaque. Opacity depends on the frequency of the light being considered. For instance, some kinds of glass, while transparent in the visual range, are largely opaque to ultraviolet light. More extreme frequency-dependence is visible in the absorption lines of cold gases.

To further decrease the likelihood that the composition will degrade and/or decompose over extended periods of time, the composition should avoid, when feasible: excessive exposure to direct sunlight, excessive heat and/or elevated temperatures. As such, in specific embodiments, the enclosed container of the kit can include printed indicia, with instructions to avoid excessive heat, elevated temperatures, direct sunlight, or a combination thereof.

Over extended periods of time, hydrogen peroxide and/or peracetic acid present in the composition will be susceptible to degrade or decompose (and a portion of the hydrogen peroxide may degrade or decompose), thereby evolving oxygen.

In specific embodiments, the enclosed container includes a head space, pressure valve, or combination thereof. In specific embodiments, the enclosed container includes a pressure valve, configured to release excessive gas from within the enclosed container. The presence of a head space and pressure valve in the container will allow for the escape of gas (e.g., oxygen) from the enclosed container, without the likelihood that the container will explode from the elevated pressure that would otherwise develop.

The term "head space" refers to a portion of the inside of a container that is not occupied by the liquid contents of the container. In particular, when a container includes a liquid composition, a head space can be present in the container such that a portion of the inside of the container does not include liquid composition, but instead includes a gas or vacuum. In specific embodiments, the head space can include oxygen ($O_2$), peracetic acid and/or acetic acid vapor. In further specific embodiments, the head space can be present in up to about 20% (v/v) of the inside of the enclosed container.

The term "pressure valve" refers to a mechanical device that will permit for the passage of gas and not fluid, preferably in one direction only, for example, exiting a container housing the pressure valve, and not entering the container.

The cleaning solution(s) described herein can be used to effectively reduce the number of microbes located upon a substrate. In specific embodiments, the composition can effectively kill and/or inhibit a microorganism (e.g., virus, fungus, mold, slime mold, algae, yeast, mushroom and/or bacterium), thereby disinfecting the substrate.

In additional specific embodiments, the composition can effectively sanitize a substrate, thereby simultaneously cleaning and disinfecting the substrate. In additional specific embodiments, the composition can effectively kill or inhibit all forms of life, not just microorganisms, thereby acting as a biocide.

In specific embodiments, the composition can effectively disinfectant a substrate. In further specific embodiments, the composition can effectively disinfectant the surface of a substrate. In additional specific embodiments, the composition can effectively sterilize a substrate. In further specific embodiments, the composition can effectively sterilize the surface of a substrate.

The term "microbe," "microbes" "microorganism," or "micro-organism" refers to a microscopic organism that comprises either a single cell (unicellular), cell clusters, or no cell at all (acellular). Microorganisms are very diverse; they include bacteria, fungi, archaea, and protists; microscopic plants (green algae); and animals such as plankton and the planarian. Some microbiologists also include viruses, but others consider these as non-living. Most microorganisms are unicellular (single-celled), but this is not universal, since some multicellular organisms are microscopic, while some unicellular protists and bacteria, like *Thiomargarita namibiensis*, are macroscopic and visible to the naked eye.

The term "virus" refers to a small infectious agent that can replicate only inside the living cells of organisms. Virus particles (known as virions) consist of two or three parts: the genetic material made from either DNA or RNA, long molecules that carry genetic information; a protein coat that protects these genes; and in some cases an envelope of lipids that surrounds the protein coat when they are outside a cell. The shapes of viruses range from simple helical and icosahedral forms to more complex structures. The average virus is about one one-hundredth the size of the average bacterium. An enormous variety of genomic structures can be seen among viral species; as a group they contain more structural genomic diversity than plants, animals, archaea, or bacteria. There are millions of different types of viruses, although only about 5,000 of them have been described in detail. A virus has either DNA or RNA genes and is called a DNA virus or a RNA virus respectively. The vast majority of viruses have RNA genomes. Plant viruses tend to have single-stranded RNA genomes and bacteriophages tend to have double-stranded DNA genomes.

The term "fungi" or "fungus" refers to a large and diverse group of eucaryotic microorganisms whose cells contain a nucleus, vacuoles, and mitochondria. Fungi include algae, molds, yeasts, mushrooms, and slime molds. See, Biology of Microorganisms, T. Brock and M. Madigan, 6th Ed., 1991, Prentice Hill (Englewood Cliffs, N.J.). Exemplary fungi include Ascomycetes (e.g., Neurospora, *Saccharomyces*, Morchella), Basidiomycetes (e.g., Amanita, Agaricus), Zygomycetes (e.g., Mucor, Rhizopus), Oomycetes (e.g., Allomyces), and Deuteromycetes (e.g., Penicillium, Aspergillus).

The term "mold" refers to a filamentous fungus, generally a circular colony that may be cottony, wooly, etc. or glabrous, but with filaments not organized into large fruiting bodies, such as mushrooms. See, e.g., Stedman's Medical Dictionary, 25th Ed., Williams & Wilkins, 1990 (Baltimore, Md.). One exemplary mold is the Basidiomycetes called wood-rotting fungi. Two types of wood-rotting fungi are the white rot and the brown rot. An ecological activity of many fungi, especially members of the Basidiomycetes is the decomposition of wood, paper, cloth, and other products derived from natural sources. Basidiomycetes that attack these products are able to utilize cellulose or lignin as carbon and energy sources. Lignin is a complex polymer in which the building blocks are phenolic compounds. It is an important constituent of woody plants. The decomposition of lignin in nature occurs almost exclusively through the agency of these wood-rotting fungi. Brown rot attacks and decomposes the cellulose and the lignin is left unchanged. White rot attacks and decomposes both cellulose and lignin. See, Biology of Microorganisms, T. Brock and M. Madigan, 6th Ed., 1991, Prentice Hill (Englewood Cliffs, N.J.).

The term "slime molds" refers to nonphototrophic eucaryotic microorganisms that have some similarity to both fungi and protozoa. The slime molds can be divided into two groups, the cellular slime molds, whose vegetative forms are composed of single amoeba like cells, and the acellular slime molds, whose vegative forms are naked masses of protoplasms of indefinite size and shape called plasmodia. Slime molds live primarily on decaying plant matter, such as wood, paper, and cloth. See, Biology of Microorganisms, T. Brock and M. Madigan, 6th Ed., 1991, Prentice Hill (Englewood Cliffs, N.J.).

The term "algae" refers to a large and diverse assemblage of eucaryotic organisms that contain chlorophyll and carry out oxygenic photosynthesis. See, Biology of Microorganisms, T. Brock and M. Madigan, 6th Ed., 1991, Prentice Hill (Englewood Cliffs, N.J.). Exemplary algae include Green Algae (e.g., Chlamydomonas), Euglenids (e.g., Euglena), Golden Brown Algae (e.g., Navicula), Brown Algae (e.g., Laminaria), Dinoflagellates (e.g., Gonyaulax), and Red Algae (e.g., Polisiphonia).

The term "yeast" refers to unicellular fungi, most of which are classified with the Ascomytes. See, Biology of Microorganisms, T. Brock and M. Madigan, 6th Ed., 1991, Prentice Hill (Englewood Cliffs, N.J.).

The term "mushrooms" refer to filamentous fungi that are typically from large structures called fruiting bodies, the edible part of the mushroom. See, Biology of Microorganisms, T. Brock and M. Madigan, 6th Ed., 1991, Prentice Hill (Englewood Cliffs, N.J.).

The term "bacterium" or "bacteria" refers to a large domain of prokaryotic microorganisms. Typically a few micrometers in length, bacteria have a wide range of shapes, ranging from spheres to rods and spirals. Bacteria are present in most habitats on Earth, growing in soil, acidic hot springs, radioactive waste, water, and deep in the Earth's crust, as well as in organic matter and the live bodies of plants and animals, providing outstanding examples of mutualism in the digestive tracts of humans, termites and cockroaches. There are typically about 40 million bacterial cells in a gram of soil and a million bacterial cells in a milliliter of fresh water; in all, there are approximately five nonillion ($5 \times 10^{30}$) bacteria on Earth, forming a biomass that exceeds that of all plants and animals. Most bacteria have not been characterized, and only about half of the phyla of bacteria have species that can be grown in the laboratory.

The term "*P. aeruginosa*" or "*Pseudomonas aeruginosa*" refers to a common bacterium that can cause disease in animals, including humans. It is found in soil, water, skin flora, and most man-made environments throughout the world. It thrives not only in normal atmospheres, but also in hypoxic atmospheres, and has, thus, colonized many natural and artificial environments. It uses a wide range of organic material for food; in animals, the versatility enables the organism to infect damaged tissues or those with reduced immunity. The symptoms of such infections are generalized inflammation and sepsis. If such colonizations occur in critical body organs, such as the lungs, the urinary tract, and kidneys, the results can be fatal. Because it thrives on most surfaces, this bacterium is also found on and in medical equipment, including catheters, causing cross-infections in hospitals and clinics. It is implicated in hot-tub rash.

The term "*S. aureus*" or "*Staphylococcus aureus*" refers to a facultative anaerobic Gram-positive bacterium. It is frequently found as part of the normal skin flora on the skin and nasal passages. It is estimated that 20% of the human population are long-term carriers of *S. aureus*. *S. aureus* is the most common species of staphylococci to cause Staph infections. The reasons *S. aureus* is a successful pathogen are a combination host and bacterial immuno-evasive strategies. One of these strategies is the production of carotenoid pigment staphyloxanthin which is responsible for the characteristic golden color of *S. aureus* colonies. This pigment acts as a virulence factor, primarily being a bacterial antioxidant which helps the microbe evade the host's immune system in the form of reactive oxygen species which the host uses to kill pathogens.

*S. aureus* can cause a range of illnesses from minor skin infections, such as pimples, impetigo, boils (furuncles), cellulitis folliculitis, carbuncles, scalded skin syndrome, and abscesses, to life-threatening diseases such as pneumonia, meningitis, osteomyelitis, endocarditis, toxic shock syndrome (TSS), bacteremia, and sepsis. Its incidence is from skin, soft tissue, respiratory, bone, joint, endovascular to wound infections. It is still one of the five most common causes of nosocomial infections, often causing postsurgical wound infections. Each year, some 500,000 patients in American hospitals contract a staphylococcal infection.

Methicillin-resistant *S. aureus*, abbreviated MRSA and often pronounced "mersa" (in North America), is one of a number of greatly-feared strains of *S. aureus* which have become resistant to most antibiotics. MRSA strains are most often found associated with institutions such as hospitals, but are becoming increasingly prevalent in community-acquired infections.

The term "*E. hirae*" or "*Enterococcus hirae*" refers to a species of *Enterococcus*.

The term "*M. terrae*" or "*Mycobacterium terrae*" refers to a slow-growing species of *Mycobacterium*. It is an ungrouped member of the third Runyon (nonchromatogenic mycobacteria). It is known to cause serious skin infections, which are relatively resistant to antibiotic therapy The term "*Mycobacterium avium* complex," "*M. avium* complex" or "MAC" refers to a group of genetically related bacteria belonging to the genus *Mycobacterium*. It includes *Mycobacterium avium* and *Mycobacterium intracellulare*.

The term "*M. avium*" or "*Mycobacterium avium*" refers to a species of *Mycobacterium*.

The term "*M. intracellulare*" or "*Mycobacterium intracellulare*" refers to a species of *Mycobacterium*.

Tubing or connectors used to connect the AER to the endoscope is generally elastomeric. Suitable elastomers for the tubing or connectors are nitrile (NBR), Hypalon, Viton, silicone, PVC, EPDM, EPDM+polypropylene (as in Santoprene), polyurethane and natural rubber. Of these materials, natural rubber has the best fatigue resistance, and EPDM and Hypalon have the best chemical compatibility. Silicone is popular with water-based fluids, such as in the bio-pharma industry.

Extruded fluoropolymer tubes such as FKM (Viton, Fluorel, etc.) have good compatibility with acids, hydrocarbons, and petroleum fuels.

There are a couple of newer tubing developments that offer a broad chemical compatibility using lined tubing and fluoroelastomers.

Unless defined otherwise, all technical and scientific terms used herein have the same meanings as commonly understood by one of ordinary skill in the art to which this invention belongs. All publications and patents specifically mentioned herein are incorporated by reference in their entirety for all purposes including describing and disclosing the chemicals, instruments, statistical analyses and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

The following paragraphs enumerated consecutively from 1 through 30 provide for various aspects of the present invention. In one embodiment, in a first paragraph (1), the present invention provides a process to disinfect an endoscope comprising the steps:

attaching an endoscope to an automated endoscope reprocessing unit, wherein the endoscope has a lumen having a proximal end and a terminal end; treating the endoscope lumen with a first peracetic acid and hydrogen peroxide solution by passing the peracetic acid and hydrogen peroxide solution through the proximal end of the endoscope through to the terminal end of the endoscope to provide a second peracetic acid and hydrogen peroxide solution;

expelling the second peracetic acid and hydrogen peroxide solution from the terminal end of the endoscope through the lumen; and measuring the expelled peracetic acid and hydrogen peroxide content after treating the lumen to disinfect the endoscope with a sensor capable of measuring peracetic acid or hydrogen peroxide content.

2. The process of paragraph 1, wherein the second peracetic acid and hydrogen peroxide solution is recycled through the endoscope lumen multiple times.

3. The process of paragraphs 1 or 2, wherein the second peracetic acid and hydrogen peroxide solution is recycled through the endoscope lumen for 1 hour or less.

4. The process of paragraphs 1 through 3, wherein the sensor determines a resistively measured value of the expelled peracetic acid or hydrogen peroxide solution in comparison to a stock peracetic acid and hydrogen peroxide solution.

5. The process of paragraph 4, wherein the sensor provides a first signal if the measured value is outside a predetermined acceptable range.

6. The process of paragraph 4, wherein the sensor provides a second signal when the measured value is within a predetermined acceptable range.

7. The process of any of paragraphs 1 through 6, wherein the first peracetic acid and hydrogen peroxide solution does not contain any 1-hydroxyethlidene-1,1-diphosphonic acid.

8. The process of paragraph 1, wherein the first peracetic acid and hydrogen peroxide solution is in contact with a polymeric resin functionalized with sulfonic acid to provide a treated peracetic acid and hydrogen peroxide solution.

9. The process of any of paragraphs 1 through 6, wherein the first peracetic acid and hydrogen peroxide solution contains 1-hydroxyethlidene-1,1-diphosphonic acid.

10. The process of any of paragraphs 1 through 9, wherein the sensor is removably attached to the terminal end of the endoscope.

11. The process of paragraph 10, wherein the sensor is attached to the terminal end of the endoscope, wherein the sensor fits tightly within the lumen or around the lumen with sufficient adhesion so that processing does not dislodge the sensor during operation.

12. The process of paragraph 10, wherein the sensor is removably attached via a quick connect assembly.

13. The process of any of paragraphs 1 through 9, wherein the sensor measures the overall chemistry in a basin of the automated endoscope reprocessor.

14. The process of any of paragraphs 1 through 9, wherein the sensor measures the chemistry via a drain manifold of the automated endoscope reprocessor.

15. The process of any of paragraphs 1 through 9, wherein the sensor measures the chemistry via chemical sample port of the automated endoscope reprocessor.

16. A process to disinfect an endoscope comprising the steps:

placing an endoscope into an automated endoscope reprocessing unit, wherein the endoscope has a lumen having a proximal end and a terminal end;

treating the endoscope with a first peracetic acid and hydrogen peroxide solution; and measuring the peracetic acid and hydrogen peroxide content after treating the endoscope with a sensor capable of measuring peracetic acid or hydrogen peroxide content.

17. The process of paragraph 16, wherein the peracetic acid and hydrogen peroxide solution is recycled through the automatic endoscope reprocessor unit containing the endoscope multiple times.

18. The process of paragraphs 16 or 17, wherein the peracetic acid and hydrogen peroxide solution is recycled through the automatic endoscope reprocessing unit containing the endoscope for 1 hour or less.

19. The process of paragraphs 16 through 18, wherein the sensor determines a resistively measured value of the peracetic acid or hydrogen peroxide solution in comparison to a stock reference peracetic acid and hydrogen peroxide solution.

20. The process of paragraph 19, wherein the sensor provides a first signal if the measured value is outside a predetermined acceptable range.

21. The process of paragraph 19, wherein the sensor provides a second signal when the measured value is within a predetermined acceptable range.

22. The process of any of paragraphs 16 through 21, wherein the peracetic acid and hydrogen peroxide solution does not contain any 1-hydroxyethlidene-1,1-diphosphonic acid.

23. The process of paragraph 16, wherein the first acid and hydrogen peroxide solution is in contact with a polymeric resin functionalized with sulfonic acid to provide a treated peracetic acid and hydrogen peroxide solution.

24. The process of any of paragraphs 16 through 21, wherein the peracetic acid and hydrogen peroxide solution contains 1-hydroxyethlidene-1,1-diphosphonic acid.

25. The process of any of paragraphs 16 through 25, wherein the sensor is removably attached to the terminal end of the endoscope.

26. The process of paragraph 25, wherein the sensor is attached to the terminal end of the endoscope, wherein the sensor fits tightly within the lumen or around the lumen with sufficient adhesion so that processing does not dislodge the sensor during operation.

27. The process of paragraph 25, wherein the sensor is removably attached via a quick connect assembly.

28. The process of any of paragraphs 16 through 24, wherein the sensor measures the overall chemistry in a basin of the automated endoscope reprocessor.

29. The process of any of paragraphs 16 through 24, wherein the sensor measures the chemistry via a drain manifold of the automated endoscope reprocessor.

30. The process of any of paragraphs 16 through 25, wherein the sensor measures the chemistry via chemical sample port of the automated endoscope reprocessor.

The invention will be further described with reference to the following non-limiting Examples. It will be apparent to those skilled in the art that many changes can be made in the embodiments described without departing from the scope of the present invention. Thus the scope of the present invention should not be limited to the embodiments described in this application, but only by embodiments described by the language of the claims and the equivalents of those embodiments. Unless otherwise indicated, all percentages are by weight.

Examples

The cleaning solutions described throughout can be flushed through and about a medical device, such as an endoscope via one or more lumens by use of an AER.

It should be understood that AERs are well known in the industry and they generally include a tray or a basin in which the medical device, such as an endoscope can be placed. The basin has a top or a door. The basin has one or more ports to allow cleaning solution to be removed during operation. The basin further includes inlets through which the cleaning solution enters into the basin. In certain aspects, the cleaning solution is directed into and through the lumen of the endoscope. In other aspects, the cleaning solution is sprayed about the endoscope contained within the basin. It should also be understood that the cleaning solution can flow into the basin (and/or through the lumen) under pressure. Appropriate apparatus are available to provide a pressurized cleaning solution.

For example, the basin is equipped with a door or top which serves to seal the reprocessing basin during operation. The top can be constructed so as to provide thermal and sound proofing features. The vertical side walls and floor member of the basin can also be formed to provide thermal and sound proofing features. Materials such as, for example, plastics, steel, glass, and the like can be used to construct the basin.

The basin can be equipped with at least one or two rotating arm members. In the one embodiment, the two rotating arm members are separately rotatably and are mounted to a central portion of the bottom of the basin and the top.

The rotating arm members include a central hub sleeve that is rotatably connected around a rotating arm hub member which extends outwardly from and substantially perpendicular to the bottom of the basin. At least two counterbalanced spray arms are connected on approximate opposing sides of the central hub sleeve. Each spray arm includes a spray arm lumen. The spray arm lumen extend at least a portion of the length of the spray arms and serve to operatively connect a hub sleeve lumen defined within the central hub sleeve with a plurality of spray jets throughout the wall of the spray arms. Together the interconnected hub sleeve lumen, spray arm lumens and spray jets provide a conduit for the pressurized flow of washing, rinsing and sterilizing fluids from a rotating fluid connector, defined within the hub member, to the interior of the basin. The washing, rinsing and sterilizing fluids are provided to the rotating fluid connector by tubular conduits. Optionally, one or more of the side walls, bottom or top members of the basin can be provided with wall spray jets which are fluidly connected to the rotating fluid connector or, alternatively, to a separate fluid inlet connector. Tubular conduits used in the present invention can be formed of metal, plastic, glass and the like, as is well known in the art.

It should be understood that the cleaning solution can be heated by the AER unit if desired. Pressurization of the cleaning solution can also be controlled by known methods.

Separate connection sites can be part of the basin such that lumen of the endoscope can connected directly to the connection site (e.g., tubing or a suitable connector) which carries a cleansing solution to the lumen. By the combination of the washing the exterior portions of an endoscope with rotating jets and internal washing of the lumen with a cleansing solution, an endoscope can be disinfected and/or sterilized with an AER.

Additionally, the cleaning solution can be monitored to ensure efficacy. This can be accomplished by use of a sensor that can measure hydrogen peroxide or peracetic acid concentrations of the cleaning solution. The sensor can be located at many sites. For example, the sensor can be placed at a port associated with the basin, such as a draining or sampling port. Alternatively, the sensor can be located at the terminal portion of the endoscope that is treated with the cleaning solution. The sensor can be firmly affixed to the terminal portion of the endoscope by various means known in the art, such as where the sensor fits tightly within the lumen or around the lumen with sufficient adhesion so that processing does not dislodge the sensor during operation, via a quick connect connection or the like. In this manner, the chemistry of the cleaning solution can be monitored in contrast to a reference sample/control, such that an operator can determine when the device meets cleanliness standards. In one aspect, the sensor provides a first signal if the measured value is outside a predetermined acceptable range. In another aspect, the sensor provides a second signal when the measured value is within a predetermined acceptable range.

In one aspect, solutions of stock cleaning solution e.g., peracetic acid and hydrogen peroxide are automatically diluted in a dilution tank for subsequent use as cleaning and sterilizing agents. The apparatus is provided with a concentration sensing and warning means for determining the value of concentration dependent parameters of the stock solution and warning if that value is outside a predetermined range.

In a further aspect, a sensor is provided for measuring the resistivity of a peracetic acid-hydrogen peroxide solution comprising a spaced pair of titanium electrodes, resistivity measuring means communicating with the electrodes when the electrodes are in contact with the solution, the measuring means providing an output indicative of the resistivity of the solution, a comparison means for comparing the resistivity indicative output with a predetermined range of acceptable outputs and issuing a warning signal when said conductivity indicative output is outside said range of acceptable outputs.

In an exemplary embodiment, a stock solution of hydrogen peroxide-peracetic acid is held in a container which communicates with an optional dilution tank by means of a conduit. A valve and the conduit operate to control the flow of the stock solution into the dilution tank. Alternatively, the cleaning solution is not diluted and the dilution tank is bypassed.

The valve is controlled by a microprocessor which opens and closes the valve in accordance with a predetermined program for controlling the circulation of fluids through the AER. Spaced probes in the conduit upstream of the valve form a resistivity cell for sensing the resistivity of the fluid passing thereby. Probes are electrically connected to a resistivity measuring circuit which issues an output to the microprocessor as described below.

The tank is also provided with a connection to a vacuum or pressurization source, a fluid outlet communicating with the endoscope or endoscopes to be cleaned and a water inlet. Valves are suitably provided and controlled by the microcomputer. The tank sits on a load cell whose output is also fed into the microcomputer. The load cell provides monitoring of the volume of the fluids in dilution tank so that preprogrammed dilutions and fluid circulations may be performed by the microcomputer. For further details on the construction and operation of such a machine, the reader is referred to U.S. Pat. No. 4,517,081.

The resistivity measuring circuit preferably utilizes a constant voltage source. A constant voltage source, from, for example, a 1 KHz sine wave oscillator applies a voltage across a bipolar electrode probe assembly through a Wheatstone bridge. Suitably the bipolar probe assembly comprises two electrodes. The output of the Wheatstone bridge is fed to a differential amplifier which is provided with a gain of 10 and which converts the sensed current in the bridge circuit to a voltage proportional to the resistance across the probe assembly. The amplified signal is conditioned by feeding through a band pass filter, desirably a 2-pole filter having a center frequency of 1000 Hz and 3 db points of 500 and 1500 Hz. The conditioned signal is then sent to a rectifier. Suitably, the rectifier is a full wave rectifier circuit having a voltage gain of two and having its gain temperature compensated. The rectified signal is then fed to a non-inverting amplifier which has a gain of 2 and has a capability of offset adjustment. Next the signal passes through an analog-to-digital converter to provide an eight-bit digital converted signal. The converted signal is ultimately fed to a microcomputer where it is compared to a preprogrammed range of acceptable signal values for the stock solution. If the measured signal is within the preprogrammed range the machine will continue to operate normally. If outside the acceptable range, a machine error is indicated and an alarm signal is issued. Suitably the alarm signal triggers an audible or visual alarm and also triggers an automatic shutoff of the valve to stop flow of the stock solution into the cleaning machine.

In attempting to develop a resistivity sensor for the peroxide/peracid system it was discovered that electrode metals such as stainless steel and other metals and even conventional platinum or platinum-black electrodes were rapidly corroded by the solution and, therefore, unsuitable. Signs of corrosion appeared in a matter of minutes. However titanium metal electrodes are sufficiently inert to allow their use in relatively concentrated peroxide/peracid solutions. Titanium electrodes showed no signs of corrosion after weeks of immersion.

The electrodes are preferably titanium having a configuration of round with hemispherically shaped ends. The electrodes may conveniently be 0.25" in diameter, and spaced from center to center by about 1.0".

The resistance of the subject solutions is relatively constant over a fairly wide range of temperatures including normal ambient temperatures of about 18-25° C. Consequently, little or no correction need to be made for normal temperature variations.

It is recommended that a calibration test be prepared for the specific peracetic acid hydrogen peroxide mixture to be used to establish the curves for concentration limits that will be used to set the alarm levels in the microcomputer. See U.S. Pat. No. 5,400,818 for a more detailed description of the sensor array, the contents of which are incorporated herein by reference.

In operation a commercial peracetic acid-hydrogen peroxide concentrate is prediluted to a stock solution in the container. The dilution tank is tared with a load cell. A valve is then opened to allow the stock solution to be drawn into the dilution tank by means of the vacuum source or forced into the tank via pressurization. As the stock solution flows past the electrodes the resistance of the solution is checked by the computer to verify that it is within the preprogrammed range of acceptable values. If within the acceptable range, the stock solution is permitted to continue flowing into the dilution tank until a predetermined amount has been drawn in as indicated by the load cell, at which point the valve is closed. Water can be added to the basin by means of water inlet to dilute the stock solution to a desired hydrogen peroxide concentration depending on whether the solution is to be used respectively for initial cleaning or bactericidal sterilizing operations.

The cleaning solution is cycled through the basin and endoscope with monitoring of the peracetic acid and/or hydrogen concentration being monitored. The cleaning solution can be removed from the basin via one of the ports and monitored via a sensor. New cleaning solution can be again added to the basin and endoscope multiple times until the cleaning solution remains within range of the desired levels of hydrogen peroxide and/or peracetic acid to indicate that the cleaning or sterilization is complete. It should be understood, that when the sensor apparatus indicates that the concentration of peracetic acid and/or hydrogen peroxide is not within the predetermined limits of what is considered acceptable for disinfection or sterilization, that the cleaning solution is removed and replaced with fresh cleaning solution and the process performed as many cycles as necessary to achieve the desired level of decontamination.

Although the present invention has been described with reference to preferred embodiments, persons skilled in the art will recognize that changes may be made in form and detail without departing from the spirit and scope of the invention. All references cited throughout the specification, including those in the background, are incorporated herein in their entirety. Those skilled in the art will recognize, or be able to ascertain, using no more than routine experimentation, many equivalents to specific embodiments of the invention described specifically herein. Such equivalents are intended to be encompassed in the scope of the following claims.

What is claimed is:

1. A process to disinfect an endoscope comprising:
attaching an endoscope to an automated endoscope reprocessing unit, wherein the endoscope has a lumen having a proximal end and a terminal end;
treating the endoscope lumen with a first peracetic acid and hydrogen peroxide solution by passing the peracetic acid and hydrogen peroxide solution through the proximal end of the endoscope through to the terminal end of the endoscope to provide a second peracetic acid and hydrogen peroxide solution;
expelling the second peracetic acid and hydrogen peroxide solution from the terminal end of the endoscope through the lumen; and
measuring the expelled peracetic acid and hydrogen peroxide content after treating the lumen to disinfect the endoscope with a sensor capable of measuring a concentration of the expelled peracetic acid or hydrogen peroxide solution and comparing the concentration of the expelled peracetic acid or hydrogen peroxide solution to a predetermined range.

2. The process of claim 1, wherein the second peracetic acid and hydrogen peroxide solution is recycled through the endoscope lumen multiple times.

3. The process of claim 1, wherein the second peracetic acid and hydrogen peroxide solution is recycled through the endoscope lumen for 1 hour or less.

4. The process of claim 1, wherein the sensor determines a resistively measured value of the expelled peracetic acid or hydrogen peroxide solution in comparison to a stock peracetic acid and hydrogen peroxide solution.

5. The process of claim 1, wherein the sensor provides a first signal if a measured value of the expelled peracetic acid or hydrogen peroxide solution is outside the predetermined range.

6. The process of claim 1, wherein the sensor provides a second signal when a measured value of the expelled peracetic acid or hydrogen peroxide solution is within the predetermined range.

7. The process of claim 1, wherein the first peracetic acid and hydrogen peroxide solution does not contain any 1-hydroxyethlidene-1,1-diphosphonic acid.

8. The process of claim 1, wherein the first peracetic acid and hydrogen peroxide solution is in contact with a polymeric resin functionalized with sulfonic acid to provide a treated peracetic acid and hydrogen peroxide solution.

9. The process of claim 1, wherein the first peracetic acid and hydrogen peroxide solution contains 1-hydroxyethlidene-1, 1-diphosphonic acid.

10. The process of claim 1, wherein the sensor is removably attached to the terminal end of the endoscope.

11. The process of claim 10, wherein the sensor is attached to the terminal end of the endoscope, wherein the sensor fits tightly within the lumen or around the lumen with sufficient adhesion so that processing does not dislodge the sensor during operation.

12. The process of claim 10, wherein the sensor is removably attached via a quick connect assembly.

13. The process of claim 1, wherein the sensor measures the overall chemistry in a basin of the automated endoscope reprocessing unit.

14. The process of claim 1, wherein the sensor measures the chemistry via a drain manifold of the automated endoscope reprocessing unit.

15. The process of claim 1, wherein the sensor measures the chemistry via chemical sample port of the automated endoscope reprocessing unit.

16. A process to disinfect an endoscope comprising:
placing an endoscope into an automated endoscope reprocessing unit; wherein the endoscope has a lumen having a proximal end and a terminal end;
treating the endoscope with a peracetic acid and hydrogen peroxide solution; and
measuring the peracetic acid and hydrogen peroxide content with a sensor after treating the endoscope, the sensor capable of measuring a concentration of the peracetic acid or hydrogen peroxide solution after treating the endoscope, and the sensor further capable of comparing the concentration of the peracetic acid or hydrogen peroxide solution to a predetermined range after treating the endoscope.

17. The process of claim 16, wherein the sensor determines a resistively measured value of the peracetic acid or hydrogen peroxide solution in comparison to a stock reference peracetic acid and hydrogen peroxide solution.

18. The process of claim 16, wherein the sensor is removably attached to the terminal end of the endoscope.

19. The process of claim 18, wherein the sensor is attached to the terminal end of the endoscope, wherein the sensor fits tightly within the lumen or around the lumen with sufficient adhesion so that processing does not dislodge the sensor during operation.

20. The process of claim 18, wherein the sensor is removably attached via a quick connect assembly.

* * * * *